US006288852B1

(12) United States Patent
Cameron

(10) Patent No.: US 6,288,852 B1
(45) Date of Patent: Sep. 11, 2001

(54) METHOD AND APPARATUS FOR RETAINING A CONTACT LENS

(76) Inventor: Robert Cameron, 3245 W. Bellwood La., Glenview, IL (US) 60025

( * ) Notice: Subject to any disclaimer, the term of this patent is extended or adjusted under 35 U.S.C. 154(b) by 0 days.

(21) Appl. No.: 09/454,434

(22) Filed: Dec. 3, 1999

Related U.S. Application Data

(60) Provisional application No. 60/110,856, filed on Dec. 4, 1998.

(51) Int. Cl.[7] .................................. G02B 7/02; A61F 9/00
(52) U.S. Cl. ............................................... 359/819; 294/1.2
(58) Field of Search ............................ 359/819; 351/178; 294/1.2

(56) References Cited

U.S. PATENT DOCUMENTS 3,304,113 * 2/1967 Hutchison ............................. 294/1.2
3,879,076 * 4/1975 Barnett ................................. 294/1.2
3,897,968 * 8/1975 Allen, Jr. .............................. 294/1.2
4,164,099 * 8/1979 Grant .
4,193,622 * 3/1980 Overman ............................... 294/1.2

FOREIGN PATENT DOCUMENTS

3822654 A1 * 1/1990 (DE) .

* cited by examiner

*Primary Examiner*—Ricky Mack
(74) *Attorney, Agent, or Firm*—Robert L. Marsh

(57) ABSTRACT

A contact lens is retained on the end of a generally cylindrical mounting member having a hemispherical upper surface shaped to receive the contact lens. The mounting member has a central opening and a plurality of small capillaries extending to the hemispherical upper surface. A vacuum is drawn through the central opening and the capillaries to retain a contact lens to the upper surface of the mounting member.

5 Claims, 3 Drawing Sheets

METHOD AND APPARATUS FOR RETAINING A CONTACT LENS

The applicant claims priority from his provisional application filed Dec. 4, 1998 gas Ser. No. 60/110,856 for the same invention. The present invention relates to the retaining of contact lens so that color or another treatment may be applied to the surface thereof.

BACKGROUND OF THE INVENTION

Contact lenses are made by curing a liquid monomer in a mold and thereafter breaking the mold to remove the hardened lens, or by machining the lens out of a plastic block. When a color is imparted to the lens, the lens can alter the color of the eyes to which they are applied. The ink which imparts the color can irritate the eye and, therefore, it is desirable to color the outer surface of the lens and not the inner surface. One method of applying color to a contact lens is to deposit a coating of ink on the portion of the mold which forms the convex surface of the lens before the liquid monomer is inserted. As the liquid monomer hardens, it bonds with the ink thereby imparting color to the lens.

If the coloring is not to be applied to the contact lens within the mold, it must be applied after the lens has been manufactured. It has been found that when a mold is broken to remove a molded lens that the lens tends to remain in the concave side of the mold leaving exposed the concave side of the lens. Since it is desirable to apply the ink to the convex surface, the lens must be entirely removed from the mold before the coloring is applied. A method has been developed whereby the concave surface of the mold can be treated with a substance which changes the surface energy of the convex side of the lens such that when a treated mold is broken to remove the lens, the concave portion of the lens will be retained in the convex portion of the mold leaving the convex surface of the lens exposed. The portion of the mold retaining the lens can, therefore, be used to handle the lens during the coloring process.

There presently is no suitable method for handling a contact lens for applying a color thereto where the lens is machine manufactured on a mandrel or the lens is molded and the technologies of coloring within the mold, or changing the surface energy of the convex surface are not available. It is the intent of the present invention to provide a method and apparatus whereby such a contact lens can be retrained for applying color thereto without employing either of the above described technologies.

SUMMARY OF THE INVENTION

Briefly, the present invention is embodied in a generally cylindrical mounting member having a hemispherical upper surface shaped to receive a contact lens. The mounting member has a central opening and a plurality of small capillaries extending to the hemispherical upper surface. A vacuum is drawn through the central opening and the capillaries to retain a contact lens to the upper surface of the mounting member.

BRIEF DESCRIPTION OF THE DRAWINGS

A better understanding of the invention will be had after a reading of the following detailed description taken in conjunction with the following detailed description wherein.

DETAILED DESCRIPTION OF THE PREFERRED EMBODIMENT

Figure 1:
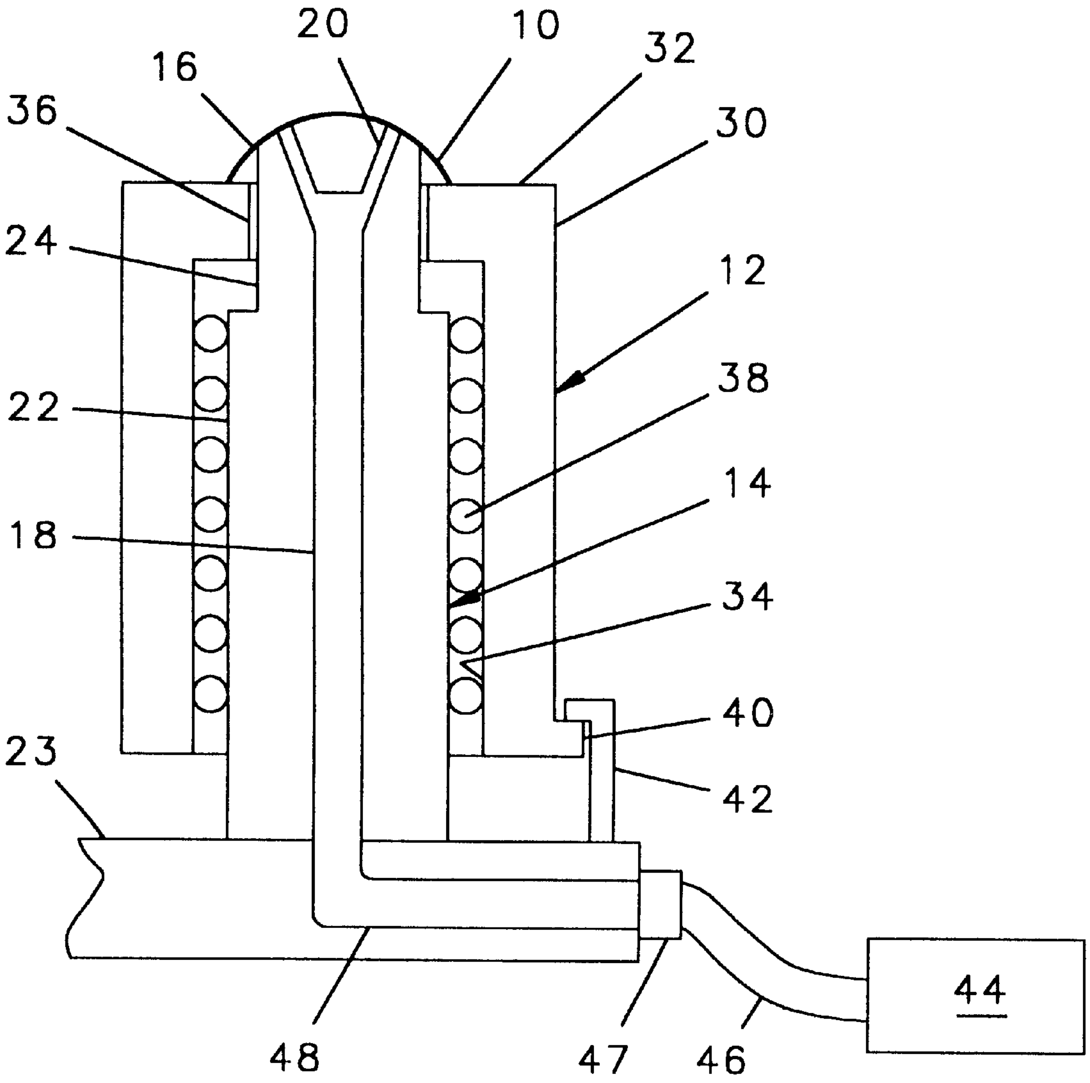
FIG. 1 is a cross sectional view of a first embodiment of the mounting device with the lens being positioned on the device.
Figure 2:
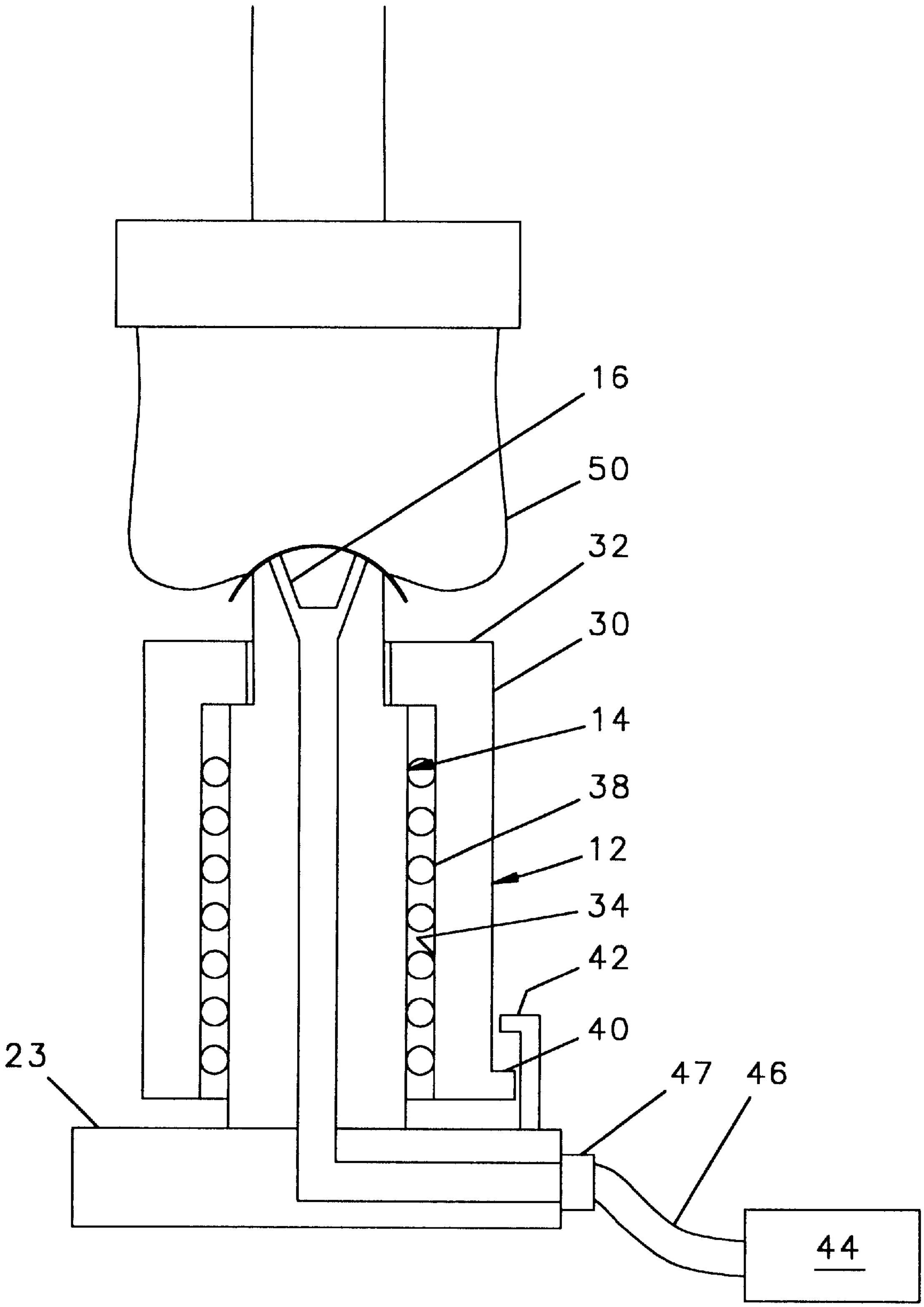
FIG. 2 is a cross sectional view of the mounting device shown in FIG. 1 retaining a lens while receiving coloring to the outer surface thereof.

Referring to FIGS. 1 and 2, to apply a coloring to the convex surface of a contact lens 10, a mounting assembly 12 in accordance with the present invention is provided. The mounting assembly 12 includes a tubular post 14 having a partial hemispherical upper surface 16 shaped complimentary to abuting concave surface of the lens 10 as shown. The post 14 has a bore 18 extending through the length thereof which narrows near the upper surface 16. A plurality of smaller capillary bores 20—20 extend from several positions around the hemispherical upper surface 16 into the central bore 18.

The post 14 has a generally cylindrical lower portion 22 having a first diameter which is mounted on the upper surface of a base 23. Above the lower portion 22 is a cylindrical upper portion 24 having a second diameter 26. As can be seen, the second diameter 26 is a littler smaller than the diameter 28 of the contact lens 10. Surrounding the post 14 is a tubular sleeve 30 having a generally planar upper surface 32 and a central bore 34. In the proximity of the upper surface 32, the central bore 34 has a neck 36, the inner diameter of which is a little larger than the second diameter of the tubular post 14 such that the neck 36 is slideable around the upper portion 24 of the post 14.

Positioned around the outer surface of the lower portion 22 of the post and within the inner surface 32 of the sleeve 30 is a preloaded ball bearing sleeve 38 which facilitates the smooth movement of the sleeve 32 upwardly and downwardly without incurring undesirable wobble as the neck 36 moves along the upper portion 22 of the post 14. At the lower end of the sleeve 30 is a stop 40 that engages a catch 42 retained on a mounting surface 21. The stop 40 and the catch 42 limit the upward movement of the sleeve 30 along the post 14. When the stop 40 is engaged with the catch 42, the planar upper surface 32 of the sleeve 30 is adjacent to the outer edge of the hemispherical upper surface 15 of the post 14. As can be seen in FIG. 1, the hemispherical surface 16 is adapted to receive a contact lens 10 and the outer edges thereof will abut against the planar surface 32 thereby aligning the lens 10 on the surface 16.

In accordance with the invention, a vacuum pump 44 is provided having a tubular vacuum line 46 which is connected to a connector 47 on the base 23. A channel 48 extends through the base 23 between the bore 18 and the connector 47 for receiving the vacuum line 46 such that the vacuum is drawn through the line 46, the channel 48, and the base 18. The vacuum pump 44 can, therefore, draw a vacuum within the bore 18 to retain the contact lens 10 to the surface 16.

Once the contact lens 10 is centered upon the upper surface 16 of the post 14, the sleeve 30 can be moved downwardly around the post to the position shown in FIG. 2 leaving the upper portion 24 of the post 14 extending above the neck 36. When the mounting assembly 12 is in this configuration with the contact lens 10 retained on the upper surface 16, the convex surface of the lens 10 can receive the application of a coloring thereto from an applicator 50.

Existing methods for applying coloring to contact lenses require an applicator 50 which applies force to the lens thereby causing alternations to the configuration of the lens 10. The moveable sleeve 30 permit the planar upper surface 32 to move away from the lower edge of the lens 10 to allow the lens 10 to expand under pressure without damaging the outer edge thereof. It should further be appreciated that since the outer diameter of the upper portion 24 of the post is less than the outer diameter of the lens 10, the forces applied to the lens during the application of a coloring will not be applied to the outer edges of the lens 10 and, therefore, those forces will not cause damage to the edges thereof.

After coloring has been applied to the upper surface of the lens 10, the vacuum within the bore 18 can be released either by opening a valve to the ambient or by turning off the pump 44, such that the lens 10 can be removed from the upper surface 16.

Figure 3:
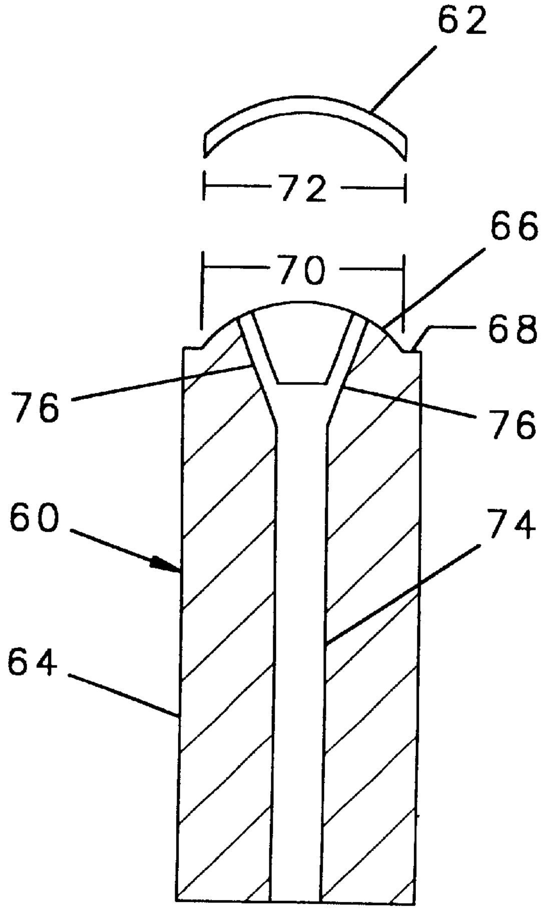
FIG. 3 is a cross sectional view of a second embodiment of a mounting device with a contact lens ready to mount thereon.
Figure 4:
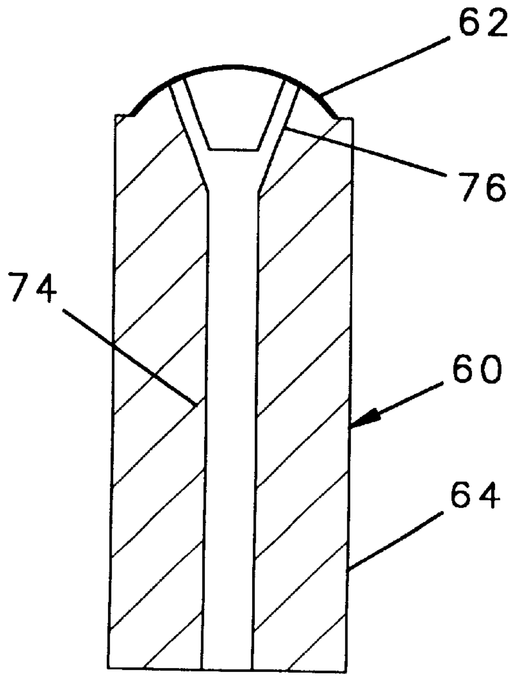
FIG. 4 is a cross sectional view of the mounting device shown in FIG. 3 with the lens retained thereon.

Referring to FIGS. 3 and 4, a second embodiment of a mounting 60 for retaining a contact lens 62 thereon comprises a generally cylindrical post 64 having a partially hemispherical upper surface 66 shaped to receive the concave side of the contact lens 62. Around the outer circumference of the hemispherical upper surface 66 is a radial shoulder 68. The outer circumference of the hemispherical upper surface has a diameter 70 which is a little larger than the outer diameter 72 of a contact lens 62 such that the lens 62 will rest upon the surface 66 with the outer edge thereof in near proximity to the radial shoulder 68 as shown in FIG. 4.

Extending longitudinally through the mounting 60 is a hollow central bore 74 and at the upper end of the mounting 60 are a plurality of small capillaries 76—76. To retain the lens 62 to the upper surface 66, a pump, not shown, is attached to draw a vacuum through the central bore 74 and the capillaries 76—76 as described with respect to the first embodiment. It should be appreciated that the outer diameter 70 of the upper surface 66 is sufficiently large to accommodate the deformation of the lens 62 when ink is being printed on the surface thereof While the present invention has been described with respect to two embodiments, it will be appreciated that many modifications and variations may be made without departing from the true spirit and cope of the invention. It is therefore the intent of the appended claims to cover all such modifications and variations that fall within the true spirit and scope of the invention.

What is claimed:

1. A mounting for a contact lens having a semi spherical surface and a circular outer edge, said mounting comprising a mounting body having a mounting surface, said mounting surface complementary to said semi spherical surface of contact lens, a plurality of capillaries extending through said mounting body to said mounting surface, means for drawing a vacuum through said capillaries to retain said semi spherical surface to said mounting surface, a sleeve surrounding said mounting body, said sleeve having a planar end surface, and one of said mounting body and said sleeve moveable with respect to the other.

2. The mounting of claim 1 and further comprising stopping means for limiting movement of said sleeve with respect to said mounting body.

3. The mounting of claim 2 wherein said mounting surface has a circular outer edge, and said stopping means limits movements of said sleeve with respect to said mounting body by stopping said movement where said planar surface is adjusted to said outer edge of said mounting surface.

4. The mounting of claim 3 and further comprising a bearing to facilitate the smooth movement of said sleeve with respect to said mounting body.

5. A mounting for a contact lens having a concave semi spherical surface having a circular outer edge with a given diameter, said mounting comprising a mounting body having a mounting surface, said mounting surface being convex semi spherical and complementary to said concave semi spherical surface of said contact lens, a plurality of capillaries extending through said mounting body to said mounting surface, means for drawing a vacuum through said capillaries to retain said concave semi spherical surface to said mounting surface, said mounting surface having a circular outer edge and having a diameter a little larger than said given diameter of said contact lens, and a radial shoulder surrounding said circular outer edge of said mounting surface.

* * * * *